United States Patent [19]

Nishikata et al.

[11] Patent Number: 5,726,317
[45] Date of Patent: Mar. 10, 1998

[54] CYCLOBUTENEDIONE COMPOUNDS

[75] Inventors: Yasunari Nishikata; Lyong Sun Pu, both of Ashigarakami, Japan

[73] Assignee: Fuji Xerox Co., Ltd., Tokyo, Japan

[21] Appl. No.: 706,778

[22] Filed: Sep. 3, 1996

[30] Foreign Application Priority Data

Sep. 5, 1995 [JP] Japan ................................. 7-228389
Sep. 13, 1995 [JP] Japan ................................. 7-235571

[51] Int. Cl.$^6$ ..................... C07D 213/02; C07C 225/20
[52] U.S. Cl. .......................................... 546/340; 564/307
[58] Field of Search .............................. 546/340; 564/307

[56] References Cited

U.S. PATENT DOCUMENTS 5,106,997  4/1992  Pu ............................................. 548/552
5,210,302  5/1993  Pu ............................................. 564/307

FOREIGN PATENT DOCUMENTS

A-3-112950   5/1991   Japan.
A-7-309818  11/1995   Japan.
A-7-309819  11/1995   Japan.
A-8-119914   5/1996   Japan.

*Primary Examiner*—Zinna Northington Davis
*Attorney, Agent, or Firm*—Oliff & Berridge, P.L.C.

[57] ABSTRACT

A cyclobutenedione derivative. It comprises substituted or non-substituted aromatic group A; conjugated chain B which may contain an aromatic bonding group; and hydrogen bonding or ion bonding cyclobutenedionyl group C having an aromatic group which is bonded to the conjugated chain B, wherein A and B and C are bonded in the form of A—B—C. Crystal of the derivative is used as a non-linear optical device.

10 Claims, 1 Drawing Sheet

CYCLOBUTENEDIONE COMPOUNDS

BACKGROUND OF THE INVENTION

1. Field of the Invention

The present invention relates to a novel cyclobutenedione derivative that is advantageous to serve as a non-linear optical material, a manufacturing method therefor and a non-linear optical device using the same.

2. Description of Related Art

In the fields of optical communication and optical information process, non-linear optical devices play important roles. Non-linear optical materials for use in the non-linear optical devices are a significantly important substance for realizing optical signal processing, such as photomixing for generating the frequency which is the sum of or the difference between two types of incident light beams having different frequencies, optical parametric generation, with which the frequency of a new generated lightwave is parametrically dependent on that of an original light source, the Pockels effect and the Kerr effect obtainable due to change in the refractive index of an optical medium, conversion of incident light into the second harmonic component (SHG) or the third harmonic component (THG) and a memory effect obtainable from optical bistability.

Hitherto, inorganic compounds have been employed as the material for the non-linear optical devices of the foregoing type. Although crystal of inorganic compounds, such as potassium titanium phosphate (KTP: KTiOPO$_4$) and lithium niobate (LN: LiNbO$_3$), has been known, characteristics required to realize the foregoing purposes have not been satisfied.

On the other hand, organic non-linear optical materials have attracted attention in recent years as new optical device materials in the optoelectronic industrial field and, thus, the materials have energetically been developed and researched. In particular, compounds of a type having electron donative groups and electron accepting groups in their $\pi$ electron conjugated system have been known to have strong optical non-linear characteristic, at the molecule level, due to the interaction of the laser beams as electromagnetic waves and $\pi$ electrons locally present in the molecules.

There have been researched, for example, 2-methyl-4-nitroaniline, m-nitroaniline, N-(4-nitrophenyl)-L-prolinol, 4-dimethylamino-4'-nitrostilbene and 4'-nitrobenzylidene-4-nitroaniline.

These materials are, similarly to inorganic materials, usually used in a single crystal state. In order to exhibit secondary non-linear optical effect in this state, it is essential that the materials do not have centrally symmetric property. However, the great dipole moment of the molecule raises a problem in that non centrally symmetric crystal cannot easily be formed as a thermodynamically stable phase.

Although a fact has been known that employment of asymmetric center and use of hydrogen bonds are effective when a material which can grow into non centrally symmetric crystal is designed, a general method has not been found yet.

Organic crystal cannot easily be allowed to grow largely and obtained organic crystal is too brittle, which are peculiar issues for organic substances; therefore, there is also a problem in that precise and fine process cannot easily be performed. Thus, there arises a requirement for a high performance material necessary to manufacture efficient devices.

In general, the non-linear optical device material is required to have great optical non-linear characteristic, excellent processability, heat resistance, stability against environment, light transparency, high dielectric breakdown voltage and stability when irradiated with a laser beam. However, conventional materials cannot satisfy these requirements.

Accordingly, the inventors of the present invention suggested cyclobutenedione derivatives represented by the following General Formula (VI) and a non-linear optical device containing the same (JP-A-3-112950). Although the suggested derivatives have a greater optical non-linear characteristic as compared with conventional materials, a further improved material having great optical non-linear characteristic has been required.

As other prior art, the following are know: JP-A-7-309818 and JP-A-7-309819, in which systhesizing method of the compound which might be similar to the compound (X) referred to in the present invention and its property are disclosed; and JP-A-8-119914, in which disclosed are the synthesizing method of the compounds (III), (V) and (VII) referred to in the present invention and properties.

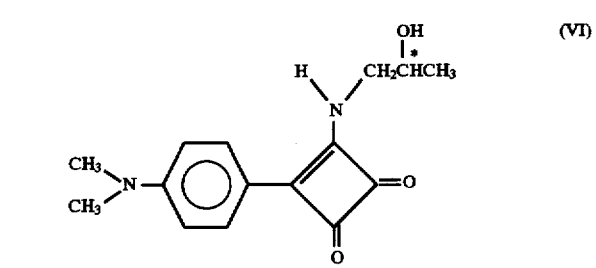

SUMMARY OF THE INVENTION

A first object of the present invention is to provide a novel chemical substance which is capable of solving the foregoing problems, which has greater non-linear optical effect, sufficient chemical and thermal stability and satisfactory transparency, which is easy to grow as single crystal from a solution state or a molten state and easy to an organic non-linear optical device.

A second object of the present invention is to provide a method of manufacturing the chemical substance of the foregoing type. A third object of the present invention is to provide a non-linear optical device containing the foregoing chemical substance.

The inventors of the present invention have found a compound exhibiting excellent secondary non-linear optical effect by inducing an appropriate substituent into a compound group exhibiting great dipolar moment of molecules, f and without the substituent capable of easily forming a centrally symmetric structure when forming crystal. Then, the inventors have applied the material to an organic non-linear optical device, and have completed the following invention.

The first aspect of the present invention is a cyclobutenedione derivative comprising: substituted or non-substituted aromatic group A; conjugated chain B which may contain an aromatic bonding group; and hydrogen bonding or ion bonding cyclobutenedionyl group C having an aromatic group which is bonded to the conjugated chain B, wherein A and B and C are bonded in the form of A—B—C.

A preferred embodiment of the above-mentioned invention is a cyclobutenedione derivative, which is represented by the following General Formula (I):

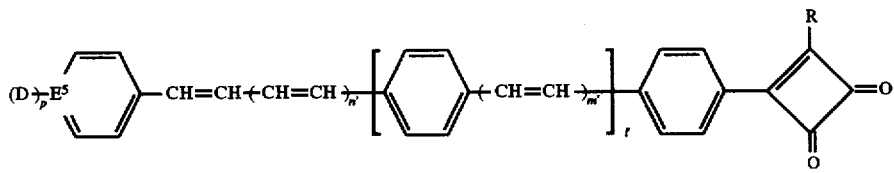

General Formula (I)

wherein p is 1 or 0, $E^5$ is a carbon atom or a nitrogen atom, in the case where $E^5$ is a carbon atom, p is 1, D is a substituent having a Hammett substituent constant $\delta_o^R$ which is 0 or a negative value, in the case where $E^5$ is a nitrogen atom, p is 0, R is a group represented by the following formula, m' is an integer 1 or 2, n' is any one of integers from 0 to 3, l' is any one of integers 0, 1 and 2, in the case where l' is 2, two m' in the formula may be the same or different from each other, and the geometric configuration of the double bond is an (E) form, a (Z) form, or a mixture of the (E) and (Z) forms,

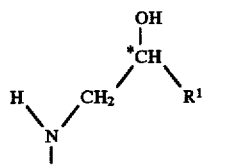

wherein $R^1$ in substituent R is an alkyl group having 1 to 4 carbon atoms and C* is an asymmetric carbon atom.

The second aspect of the invention is a method of manufacturing a cyclobutenedione derivative represented by General Formula (I), comprising the step of allowing a cyclobutenedione derivative represented by the following General Formula (III) and a compound represented by the following General Formula (IV) to react with each other:

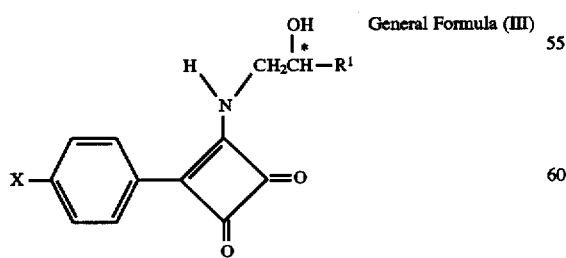

General Formula (III)

wherein X is a halogen atom, $R^1$ is an alkyl group having 1 to 4 carbon atoms and C* is an asymmetric carbon atom,

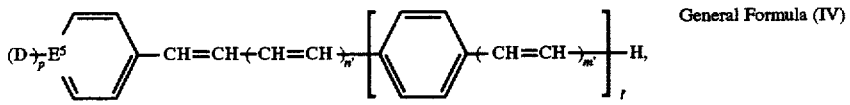

General Formula (IV)

which is an (E) form, a (Z) form, or a mixture of the (E) and (Z) forms, wherein p is 1 or 0, $E^5$ is a carbon atom or a nitrogen atom, in the case where $E^5$ is a carbon atom, p is 1, D is a substituent having a Hammett substituent constant $\delta_0^R$ which is 0 or a negative value, in the case where $E^5$ is a nitrogen atom, p is 0 or 1, when pis 1, D is an allyl group with or without substituents, and there is a suitable negative charged ion exsisting for the sake of neutrization of positive charge existing or a nitrogen atom, m' is an integer 1 or 2, n' is any one of integers from 0 to 3, l' is any one of integers 0, 1 and 2, and in the case where l' is 2, two m' in the formula may be the same of different from each other,

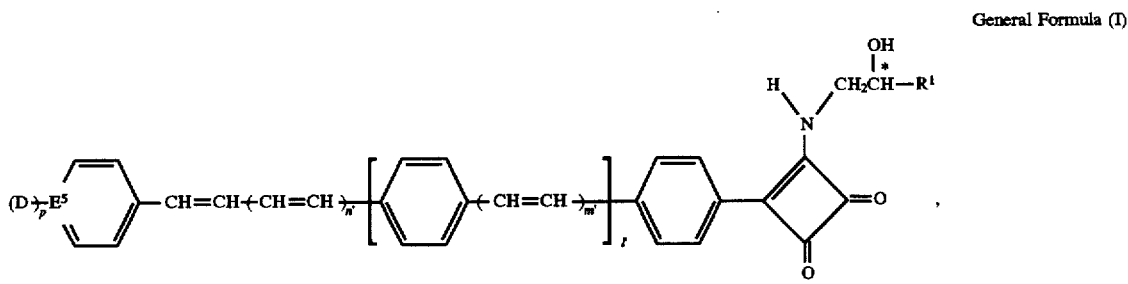

General Formula (I)

which is an (E) form, a (Z) form, or a mixture of the (E) and (Z) forms, wherein p is 1 or 0, $E^5$ is a carbon atom or a nitrogen atom, in the case where $E^5$ is a carbon atom, p is 1, D is a substituent having a Hammett substituent constant $\delta_0^R$ which is 0 or a negative value, in the case where $E^5$ is a nitrogen atom, p is 0, m' is an integer 1 or 2, n' is any one of integers from 0 to 3, l' is any one of integers 0, 1 and 2, in the case where l' is 2, two m' in the formula may be the same or different from each other, $R^1$ is an alkyl group having 1 to 4 carbon atoms and C* is an asymmetric carbon atom.

The third aspect of the invention is a method of manufacturing a cyclobutenedione derivative, comprising the steps of reacting a cyclobutenedione derivative represented by the following General Formula (VII) with a pyridine derivative represented by the following General Formula (IVa) to obtain a product represented by the following General Formula (VIII), and reacting the product with alkylhalide represented by the following General Formula (iX), thereby obtaining a cyclobutenedione derivative represented by General Formula (II):

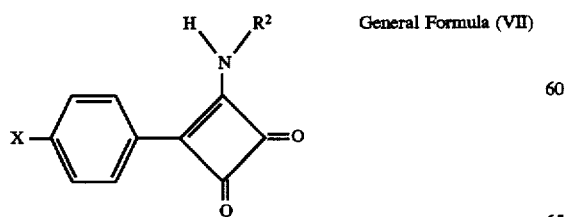

General Formula (VII)

wherein X is a halogen atom and $R^2$ is an alkyl group having 1 to 4 carbon atoms,

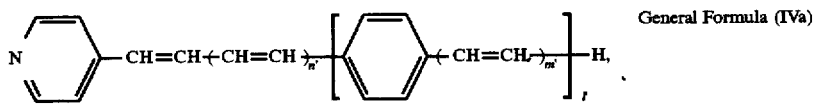
General Formula (IVa)

which is an (E) form, a (Z) form, or a mixture of the (E) and (Z) forms,
wherein m' and n' are the same as defined above.

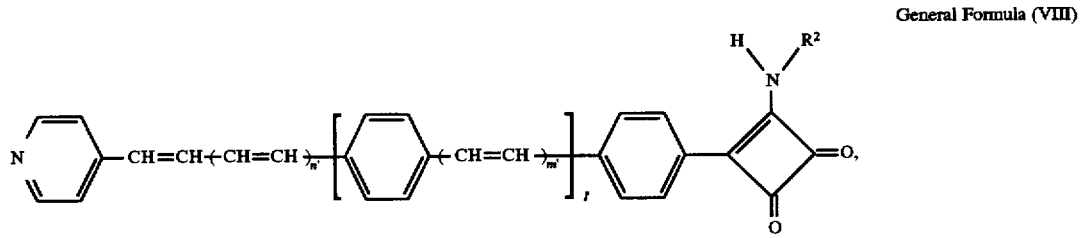
General Formula (VIII)

which is an (E) form, a (Z) form, or a mixture of the (E) and (Z) forms, wherein $R^2$ is an alkyl group having 1 to 4 carbon atoms m' is an integer 1 or 2, n' is any one of integers from 0 to 3, l' is any one of integers 0, 1 and 2, in the case where l' is 2, two m' in the formula may be the same or different from each other, General Formula (IX)

$$R^3-X$$

wherein X is a halogen atom and $R^3$ is an alkyl group having 1 to 4 carbon atoms

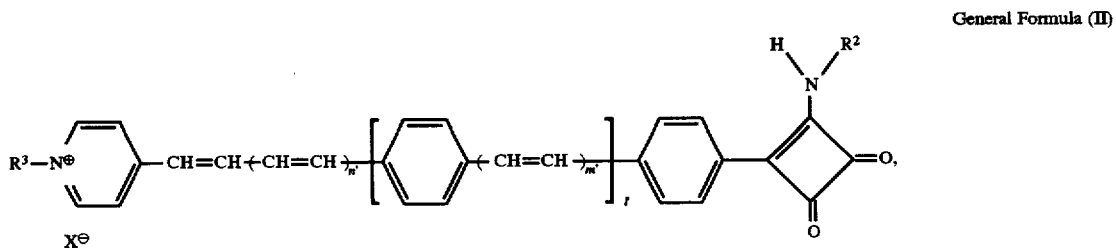
General Formula (II)

which is an (E) form, a (Z) form, or a mixture of the (E) and (Z) forms, wherein $R^2$ and $R^3$ are each independently an alkyl group having 1 to 4 carbon atoms, X is a halogen atom, m' is an integer 1 or 2, n' is any one of integers from 0 to 3, l' is any one of integers 0, 1 and 2, in the case where l' is 2, two m' in the formula may be the same or different from each other.

The fourth aspect of the invention is a non-linear optical device wherein a plurality of cyclobutenedione derivative molecules are bound, each of which is represented by the following General Formula (I):

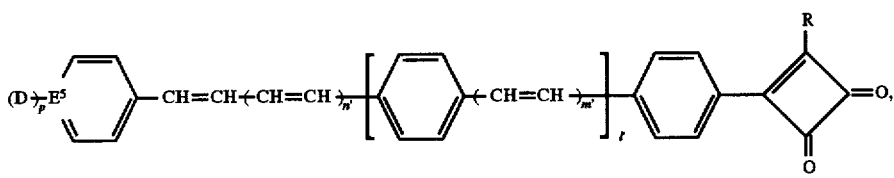

General Formula (I)

which is an (E) form, a (Z) form, or a mixture of the (E) and (Z) forms, wherein R is a group represented by the following formula, p is 1 or 0, $E^5$ is a carbon atom or a nitrogen atom, in the case where $E^5$ is a carbon atom, p is 1, D is a substituent having a Hammett substituent constant $\delta_o{}^R$ which is 0 or a negative value, in the case where $E^5$ is a nitrogen atom, p is 0, m' is an integer 1 or 2, n' is any one of integers from 0 to 3, l' is any one of integers 0, 1 and 2, in the case where l' is 2, two m' in the formula may be the same or different from each other,

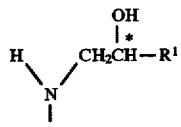

wherein $R^1$ in substituent R is an alkyl group having 1 to 4 carbon atoms and C* is an asymmetric carbon atom.

The inventors of the present invention have investigated organic compounds including the cyclobutenedione derivative previously suggested, suitable for non-linear optical devices, thereby finding that a cyclobutenedione derivative represented by in particular the foregoing formula (I) has significantly great optical non-linear characteristic as compared with conventional non-linear optical materials. Thus, the present invention has been established.

$\delta_o{}^R$ is a Hammett resonance substituent constant at the p substituent position.

D is preferably H, —$OR^2$, —$NR^3R^4$, or a halogen atom wherein $R^2$, $R^3$ and $R^4$ are each independenty H or an alkyl group having 1-4 carbon atoms. Preferably they are methyl or ethyl. —$OR^2$ includes —$OCH_3$ ($\delta_o{}^R$=−0.43). —$NR_3R^4$ includes —$N(CH_3)_2$ (−0.57), —$NH_2$(−0.51). Halogen atoms include I (−0.22), Br(−0.29), Cl(−0.31), and F(−0.48). Other substituents than the above include H(0.0) and —CN(−0.06). Preferable examples of D are H, —$OCH_3$, —$N(CH_3)_2$, Br and Cl. More preferable is —$N(CH_3)_2$, which has small a $\delta_o{}^R$ and thus a high electro donating property.

The cyclobutenedionyl group contained in the cyclobutenedione derivative expressed as A—B—C has a great interaction with π electrons in the compound and exhibits great electron absorbing characteristic due to resonant effect. Therefore, a structure in which the molecule is considerably electrically-polarized, can easily be formed, thus causing excellent optical non-linear characteristic to be realized. Since this compound has a long π electron conjugated system expressed as A—B, it exhibits significantly great optical non-linear characteristic as compared with the cyclobutenedione derivative suggested previously.

PREFERRED EMBODIMENTS OF THE INVENTION

Figure 1:
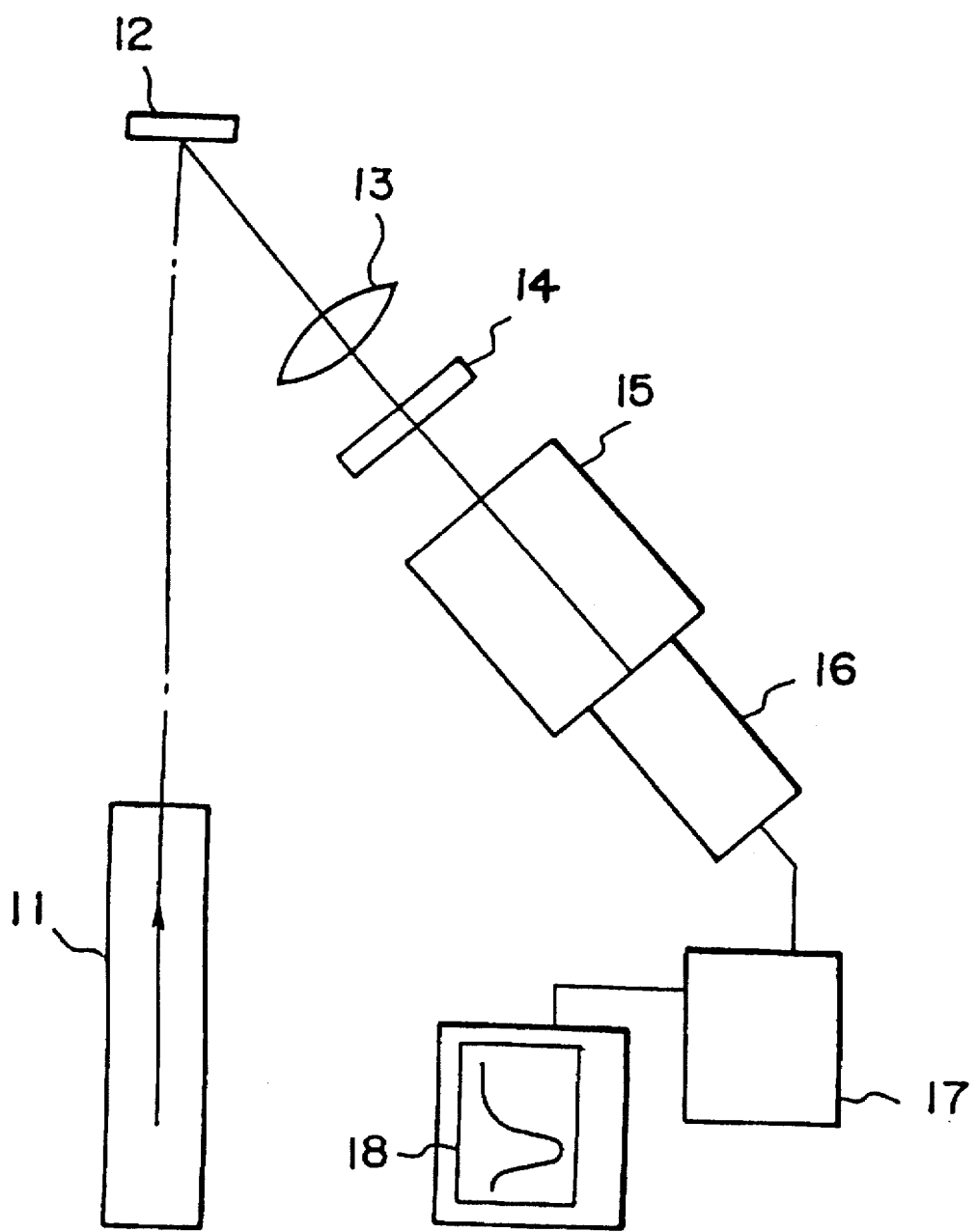
FIG. 1 is a block diagram showing an optical system for measuring the optical non-linear characteristic (the SHG activity) of samples.

In order to make the present invention effective, portion A of cyclobutenedione derivative A—B—C is defined as follows:

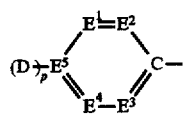

General Formula (A1)

wherein $E^1$ to $E^5$ are each independently a carbon atom permitted to have a nitrogen atom or a substituent, at least two of $E^1$ to $E^5$ are carbon atoms, in a case where adjacent $E^1$ and $E^2$ or $E^3$ and $E^4$ are carbon atoms each having a substituent, the substituents may be connected to form a ring, p is 1 or 0, in the case where $E^5$ is a carbon atom, p is 1, D is a substituent having a Hammett substituent constant $\delta_o{}^R$ which is 0 or a negative value, in the case where $E^5$ is a nitrogen atom, p is 0 or 1, in the case where p is 1, D is a substituted or a non-substituted alkyl group, it this case nitrogen atom represented by $E^5$ is positively charged. Thus, an appropriate ion having a negative charge is present as a counter ion.

When $E^5$ is a carbon atom, p is 1, and D is a substituent having the Hammett substituent constant $\delta_o{}^R$ of 0 or a negative value. This substituent raises the electron density in the overall conjugated system so that the second order hyperpolarizablity is further raised. If $E^5$ is a nitrogen, then p is 0 or 1. If p is 1, then D is a substituted or a non-substituted alkyl group. Also in this case, the effect of the unshared electron pair on the nitrogen or the electron donative characteristic of the substituted or non-substituted alkyl group bonded to the nitrogen attains an effect of further raising the second order hyperpolarizablity of the molecule.

To effectively constitute a long n electron conjugated system represented by A—B in the compound, it is effective for conjugated chain B permitted to contain the foregoing aromatic bonding group to have at least one molecule structure selected from the group consisting of materials represented by the following general formulas.

which is an (E) form, a Z) form or a mixture of the (E) and (Z) forms

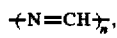

which is an (E) form, a (Z) form or a mixture of the (E) and (Z) forms

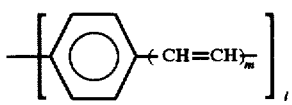

which ms an (E) form, a (Z) form or a mixture of the (E) and (Z) forms, wherein m, n and 1 are each independently the number of bonding units of the conjugated chain.

wherein R is a group represented by the following formula

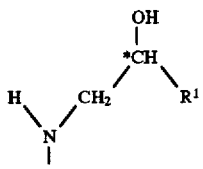

wherein $R^1$ in R is an alkyl group having 1 to 4 carbon atoms and C* is an asymmetric carbon atom.

The chemical structure represented by General Formula (2) makes it possible to greatly exhibit the optical non-linear characteristic thereof due to conjugation of the benzene ring and the cyclobutenedione structure. The chemical structure represented by R contributes to effective arrangement, in crystal, of molecules which respectively have great optical non-linear characteristic.

The cyclobutenedione derivatives having these functions include compounds represented by General Formulas (I) and (Ia):

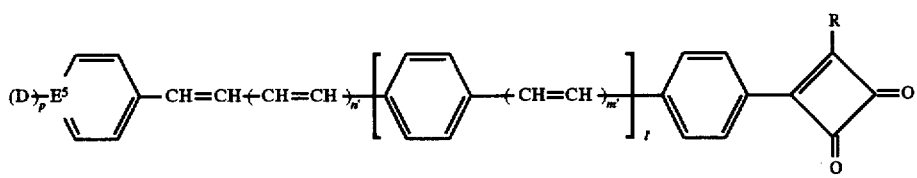

General Formula (I)

By causing hydrogen bonding or ion bonding cyclobutenedionyl group C, having an aromatic group which is bonded to the foregoing conjugated chain B, to have the structure represented by the following General Formula C1, the material is cable of effectively exhibiting the optical non-linear characteristic of the molecule.

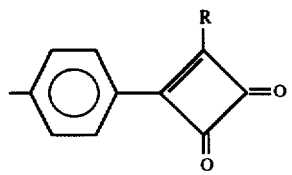

General Formula (C1)

wherein p is 1 or 0, $E^5$ is a carbon atom or a nitrogen atom, if $E^5$ is a carbon atom, then p is 1, D is a substituent having a Hammett substituent constant $\delta_0^R$ which is 0 or a negative value, if $E^5$ is a nitrogen atom, then p is 0, R is a group represented by the following formula, m' is an integer 1 or 2, n' is any one of integers from 0 to 3, l' is any one of integers 0, 1 and 2, if l' is 2, then two m' may be the same or different from each other, and the geometric configuration of the double bond is an (E) form, a (Z) form or a mixture of the (Z) and (E) forms.

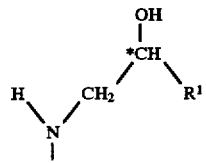

wherein $R^1$ in the substituent R is an alkyl group having 1 to 4 carbon atoms and C* is an asymmetric carbon atom.

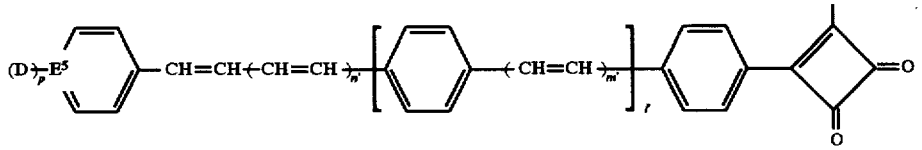

General Formula (1a)

wherein p is 1 or 0, $E^5$ is a carbon atom or a nitrogen atom, if $E^5$ is a carbon atom, then p is 1, D is a substituent having a Hammett substituent constant $\delta_o^R$ which is 0 or a qnegative value, if $E^5$ is a nitrogan atom, then p is 0, R is a group represented by the following formula, m' is an integer 1 or 2, n' is any one of integers from 0 to 3, l' is any one of integers 0, 1 and 2, if l' is 2, then two m' in the formula above may be the same or different from each other, and the geometric configuration of the double bond is an (E) form, a (Z) form or a mixture of the (Z) and (E) forms.

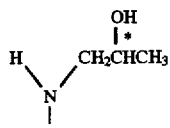

wherein $R^1$ in the substituent R is an alkyl group having 1 to 4 carbon atoms and C* is an asymmetric carbon atom.

The cyclobutenedione derivative represented by the following General Formula (II) included in General Formula (1) is an especially preferred material.

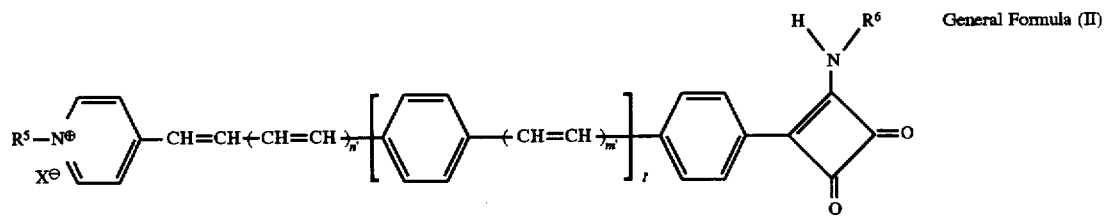

General Formula (II)

wherein $R^5$ and $R^6$ are each independently an alkyl group having 1 to 4 carbon atoms, X is a halogen atom, m' is an integer 1 or 2, n' is any one of integers from 0 to 3, l' is an integer 1 or 2, if l' is 2, then two m' in the formula above may be the same or different from each other, and geometric configuration of the double bond is an (E) form, a (Z) form or a mixture of the (Z) and (E) forms.

The compounds represented by General Formula (1) include the following compounds.

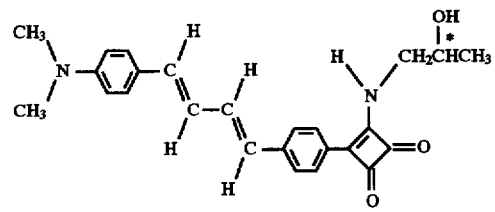

wherein C* is an asymmetric carbon atom.

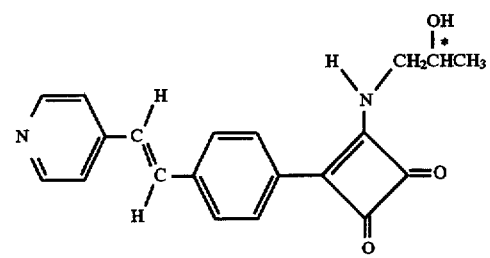

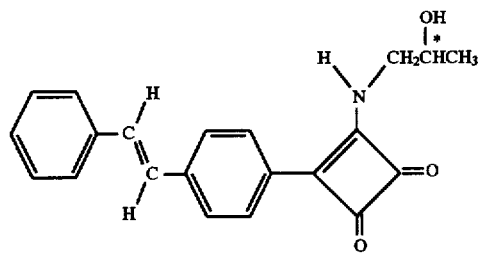

wherein C* is an asymmetric carbon atom.

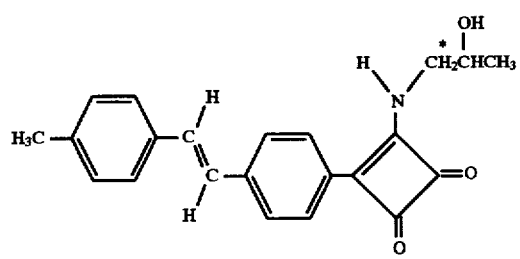

wherein C* is an asymmetric carbon atom.

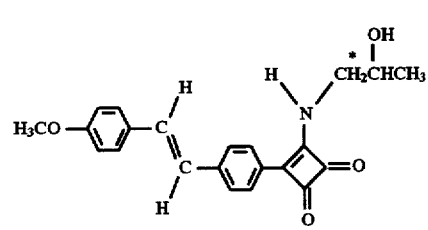

wherein C* is an asymmetric carbon atom.

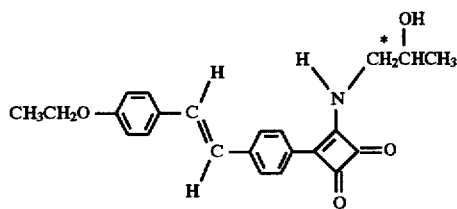

wherein C* is an asymmetric carbon atom.

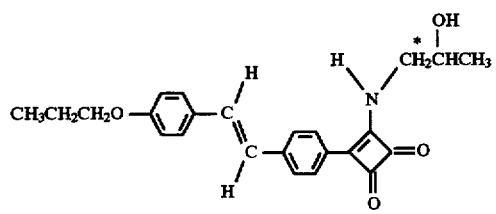

wherein C, is an asymmetric carbon atom.

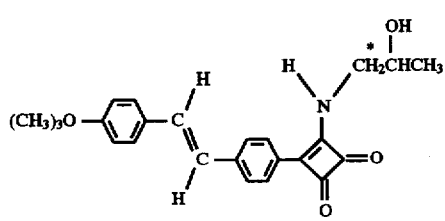

wherein C, is an asymmetric carbon atom.

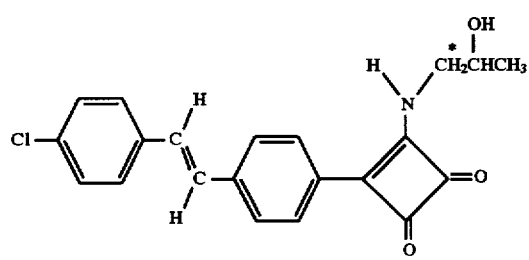

wherein C, is an asymmetric carbon atom.

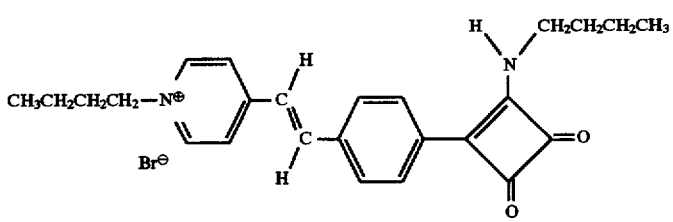

wherein C* is an asymmetric carbon atom.

The cyclobutenedionyl group contained in the cyclobutenedione derivative represented by the General Formula (I), as can be understood from the maximum absorption wavelength (the charge transfer zone in the molecule) described in Examples below, has a great interaction with π electrons in the compound and exhibits great electron absorption due to the resonance effect. Therefore, a structure in which the molecule is considerably electrically-polarized, can easily be realized, thus causing the great optical non-linear characteristic to be realized. Since this compound has a long π electron conjugated system, it has a significantly great optical non-linear characteristic (second order hyperpolarizablity β is $20 \times 10^{-30}$ esu or higher) as compared with the cyclobutenedione derivative suggested previously. Therefore, this compound is a preferred material for a non-linear optical device.

One type of the cyclobutenedione derivatives represented by the General Formula (I) has amino-alcohol having an asymmetric carbon atom serving as a substituent and introduced thereto. The stereostructure and the hydrogen bond of this substituent enables the orientation of molecules in crystal to be controlled. Thus, asymmetric molecular orientation with respect to the center is realized in a molecule of a type having a high dipole efficiency. For this reason, crystal having great optical non-linear characteristic can easily be generated.

Another type of the cyclobutenedione derivatives represented by the General Formula (I) has a quaternary pyridinium salt structure. This makes it possible to control orientation of molecules in crystal due to the ionic interaction. As a result, crystal having great optical non-linear characteristic can easily be generated.

The cyclobutenedione derivative represented by the foregoing General Formula (I) can easily be prepared by the following reaction with an excellent yield. In item A) concerned chemical formulas are illustrated, and in item B) the reaction is explained.

A)

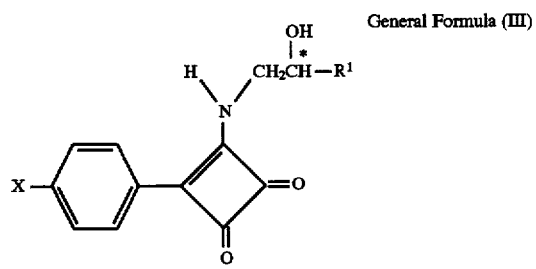

General Formula (III)

wherein X is a halogen atom, R¹ is an alkyl group having 1 to 4 carbon atoms and C* is an asymmetric carbon atom.

General Formula (IV)

which is an (E) form, a (Z) form or a mixture of the (Z) and (E) forms, wherein p is 1 or 0, $E^5$ is a carbon atom or a nitrogen atom, if $E^5$ is a carbon atom, then p is 1, D is a substituent having a Hammett substituent constant $\delta_0^R$ which is 0 or a negative value, if $E^5$ is a nitrogen atom, then p is 0, m' is an integer 1 or 2, n' is any one of integers from 0 to 3, l' is an integer 0, 1 or 2, and if l' is 2, then two m' in the formula above may be the same or different from each other.

an acid acceptor, added to the obtained solution, followed by heating and permitting reactions to take place. The palladium complex catalyst may be any one of known materials having catalyst activity with respect to the coupling reaction between an aryl halide and a diene compound, the materials including tetrakis (triphenylphosphine) palladium (0), tetrakis (tri-o-tolylphosphine) palladium (0), dichloro-bis (triphenylphosphine) palladium (II) and bis [1,2-di (diphenylphosphino) ethane] palladium (0) (R.F.Heck, "Palladium Reagents in Organic Syntheses", Academic Press, London (1985)). The quantity of the catalyst may be changed from 1/1000 equivalent to 1 equivalent with respect to the cyclobutenedione derivative represented by the foregoing General Formula (II), it is preferable that the quantity of the catalyst be in a range from 1/100 equivalent to 5/100 equivalent with respect to the cyclobutenedione derivative represented by the General Formula (II). The reason for the limitation of the preferred quantity of the catalyst is as follows. If the quantity is considerably smaller than 1/100 equivalent, the catalyst activity deteriorates. If the quantity is considerably larger than 5/100 equivalent, the product and the catalyst cannot easily be separated from each other.

Thus, the yield of the product (I) deteriorates. In place of the palladium complex catalyst, an organic or inorganic bivalent palladium compound, such as palladium chloride (II) or palladium acetate (II) and a phosphine compound, such as triphenylphosphine or tri-o-tolylphosphine or 1,2-di (diphenylphosphino) ethane, may be separately charged into the system to cause a similar reaction to proceed with a satisfactory yield. As for the quantity of the phosphine compound, the reaction generally proceeds at a maximum yield in the case where the number of phosphorus atoms is 4 to 6 equivalents with respect to palladium. However, the

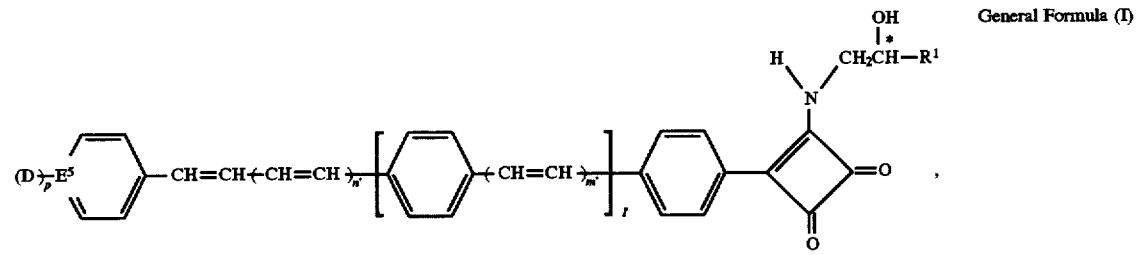

General Formula (I)

which is an (E) form, a (Z) form or a mixture of the (Z) and (E) forms, wherein p is 1 or 0, $E^5$ is a carbon atom or a nitrogen atom, if $E^5$ is a carbon atom, then p is 1, D is a substituent having a Hammett substituent constant $\delta_0^R$ which is 0 or a negative value, if $E^5$ is a nitrogen atom, then p is 0, m' is an integer 1 or 2, n' is any one of integers from 0 to 3, l' is an integer 0, 1 or 2, if l' is 2, then two m' in the formula above may be the same or different from each other. R¹ is an alkyl group having 1 to 4 carbon atoms and C* is an asymmetric carbon atom.

B) Initially, the cyclobutenedione derivative represented by the General Formula (III) is dissolved in a solvent, such as N,N-dimethylformamide, N,N-dimethylacetoamide, N-methylpyrolidone or dimethylsulfoxide. Then, compound (IV) in a little excess of the quantity of the cyclobutenedione derivative is, together with palladium complex catalyst and reaction proceeds at a satisfactory yield even if the quantity of the phosphine compound is out of the foregoing range, depending upon the type of the palladium compound. The acid acceptor may be a known acid acceptor, for example, triethylamine, tributylamine, 1,8-diaza [5,4,0] bicycloundecene-7, 1,8-bis (dimethylamino) naphthalene, potassium carbonate or sodium acetate. The most satisfactory yield is realized when the quantity of the acid acceptor is from 1.2 times to 1.5 times the quantity of the cyclobutenedione derivative represented by the foregoing General Formula (II); however, the reaction proceeds at a satisfactory yield even if the quantity of the acid acceptor is considerably larger or smaller than the foregoing quantity (even if the acid acceptor is not used, in some special cases), depending upon the combination with the catalyst. The reaction proceeds at a temperature in a range from 40° C. to 200° C. It is preferable that the reaction temperature be set to 90° C. to 120°πC. in view of realizing a satisfactory yield.

The cyclobutenedione derivative represented by the foregoing formula (I) can be also prepared easily and at a satisfactory yield by the following reaction.

A')

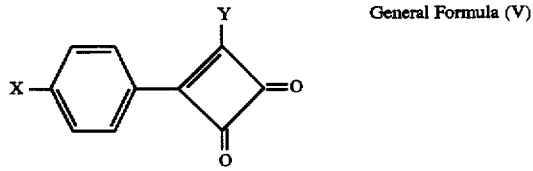

General Formula (V)

wherein X is a halogen atom, Y is a chlorine atom, a bromine atom, a methoxy group or an ethoxy group)

General Formula (VI)

wherein $R^1$ is an alkyl group having 1 to 4 carbon atoms, and C* is an asymmetric carbon atom.

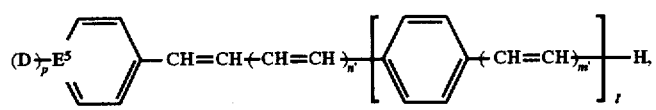

General Formula (IV)

which is an (E) form, a (Z) form or a mixture of the (E) and (Z) forms, wherein p, E, D, m', n', l', $R^1$ and C* are the same as those described above.

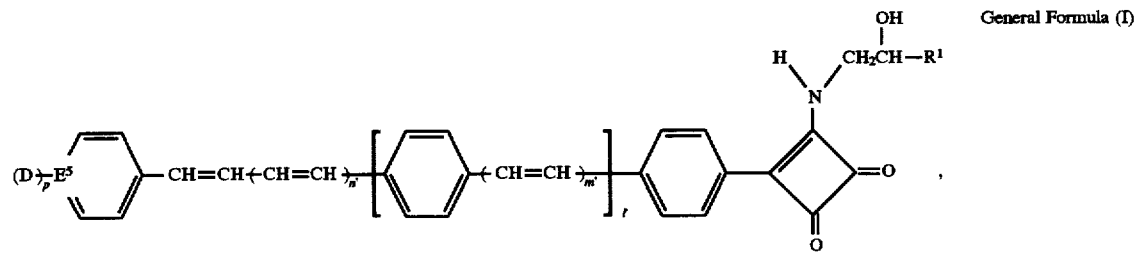

General Formula (I)

which is an (E) form, a (Z) form or a mixture of the (E) and (Z) forms B') Initially, the cyclobutenedione derivative represented by the General Formula (V) is dissolved in a solvent, such as N,N-dimethylformamide, N,N-dimethylacetoamide, N-methylpyrolidone or dimethylsulfoxide. Then, asymmetric 1-amino-2-alcohol (VI) represented by the foregoing General Formula (V) in a little excess is, while being stirred, added thereto so that the reaction is allowed to proceed.

Then, the above-mentioned (III) in a little excess with respect to the foregoing cyclobutenedione derivative is added to the obtained solution, together with the palladium complex catalyst and the acid acceptor, followed by raising the temperature so that the reaction is allowed to proceed. The type and the quantity of the palladium complex catalyst, those of the acid acceptor and the reaction temperature are the same as those described above.

The compound having the quaternary pyridinium salt structure among the compounds represented by the foregoing General Formula (I) can be prepared as follows:

A")

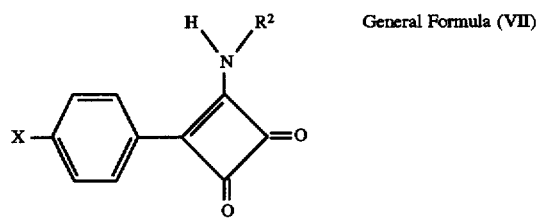

General Formula (VII)

wherein X is a halogen atom, $R^2$ is an alkyl group having 1 to 4 carbon atoms.

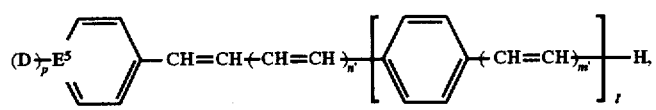

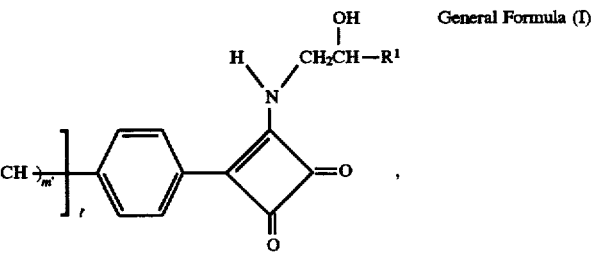

General Formula (IVa)

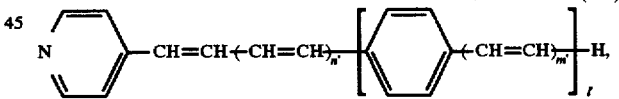

which is an (E) form, a (Z) form or a mixture of the (E) and (Z) forms, wherein m' and n' are the same as those described above.

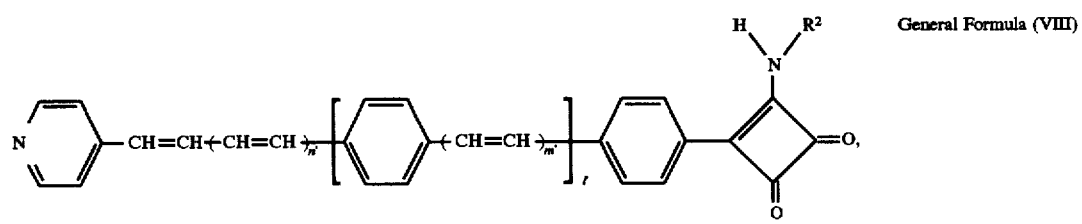

General Formula (VIII)

which is an (E) form, a (Z) form or a mixture of the (E) and (Z) forms.

wherein $R^2$ is an alkyl group having 1 to 4 carbon atoms, m is an integer l' or 2, n' is any one of integers from 0 to 3, l' is any one of integers 0, 1 and 2, and if l' is 2, two m' in the formula may be the same or different from each other.

$$R^3—X \qquad \text{General Formula (IX)}$$

wherein X is a halogen atom and $R^3$ is an alkyl group having 1 to 4 carbon atoms.

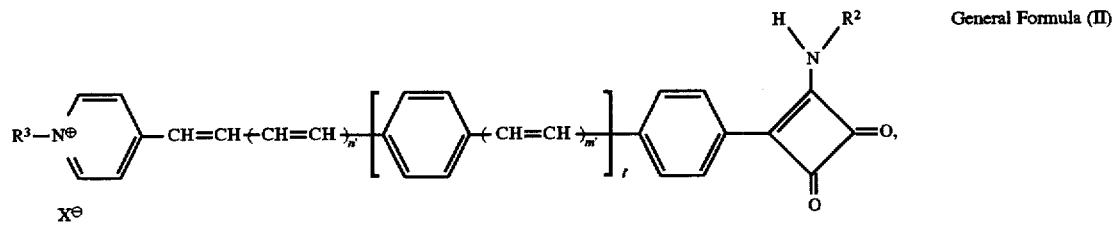

General Formula (II)

which is an (E) form a (Z) form or a mixture of the (E) and (Z) forms, wherein $R^2$ and $R^3$ are each independently an alkyl group having 1 to 4 carbon atoms, X is a halogen atom, m' is an integer 1 or 2, n' is any one of integers from 0 to 3, l' is any one of integers 0, 1 and 2, and if l' is 2, then two m' in the formula may be the same or different from each other. B") Initially, the compound represented by General Formula (VIII) is prepared from the compound represented by General Formula (VII) and the compound represented by General Formula (VIa). In this case, the reaction is performed by the same method and in the same condition as those described above.

Then, the compound represented by foregoing (VIII), alkylhalide (IX) and an acid acceptor are dissolved or suspended in a solvent, such as N,N-dimethylformamide, N,N-dimethylacetoamide, N-methylpyrolidone or dimethylsulfoxide. The overall system is heated to cause the reaction to proceed. After the reaction is completed and in a state where the system is still hot, insolubles are quickly removed by filtration, followed by allowing the system to stand still. Thus, the cyclobutenedione derivative represented by General Formula (II) can be obtained in the form of crystal. The acid acceptor may be any one of known acid acceptors including triethylamine, tributylamine, pyridine, 1,8-diaza [5,4,0] bicycloundeccene-7, 1,8-bis (dimethylamino) naphthalene, potassium carbonate or sodium acetate. The most satisfactory yield is realized when the quantity of the acid acceptor is 1.2 times to 1.5 times the quantity of the cyclobutenedione derivative represented by the foregoing General Formula (II); however, the reaction proceeds at a satisfactory yield even if the quantity of the acid acceptor is considerably larger or smaller than the foregoing quantity (even if the acid acceptor is not used, in some special cases), depending upon the combination with the catalyst. The reaction proceeds at a temperature in a range from 100° C. to 200° C. It is preferable that the reaction temperature be set to 90° C. to 120° C. in view of realizing a satisfactory yield.

According to the present invention, a non-linear optical device, wherein a plurality of cyclobutenedione derivative molecules are bound, each of which is represented by the following General Formula (I) is also provided.

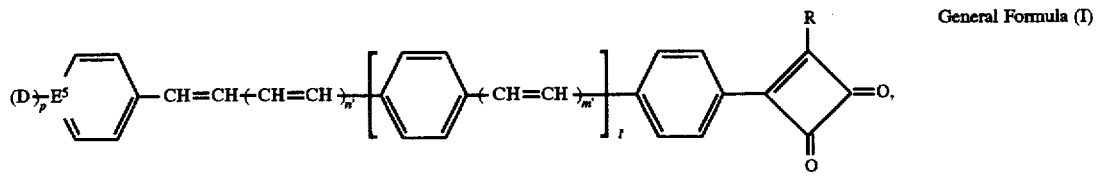

General Formula (I)

which is an (E) form, a (Z) form or a mixture of the (E) and (Z) forms, wherein R is a group represented by the following formula, p is 1 or 0, $E^5$ is a carbon atom or a nitrogen atom, if $E^5$ is the carbon atom, then p is 1, D is a substituent having a substituent constant of 0 or a negative value, if $E^5$ is a nitrogen atom, then p is 0, m' is an integer 1 or 2, n' is any one of integers from 0 to 3, l' is any one of integers 0, 1 and 2, and if l' is 2, m' in the formula may be the same or different from each other.

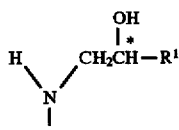

wherein $R^1$ in substituent R is an alkyl group having 1 to 4 carbon atoms and C. is an asymmetric carbon atom.

A preferred form is as follows:

(i) A non-linear optical device wherein a plurality of the cyclobutenedione derivative molecules are bound, each of which is represented by the following General Formula (II)

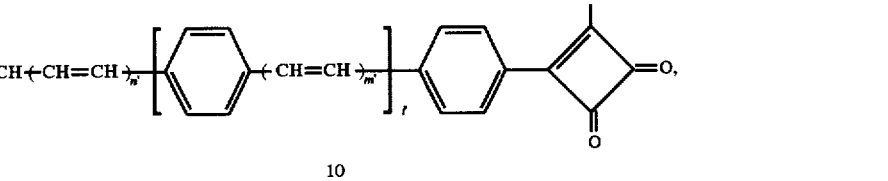

General Formula (II)

which is an (E) form, a (Z) form or a mixture of the (E) and (Z) forms, wherein $R^5$ and $R^6$ are each independently an alkyl group having 1 to 4 carbon atoms, X is a halogen atom, m' is an integer 1 or 2, n' is any one of integers from 0 to 3, l' is any one of integers 0, 1 and 2, and if l' is 2, two m' in the formula may be the same of different from each other.

(ii) A non-linear optical device, which comprises crystal having a non centrally symmetric structure formed by hydrogen-bonding of molecules of a compound which is represented by the following General Formula (I) and which has a substituent capable of hydrogen-bonding in the 2-position of its cyclobutenedionyl group, through the substituent:

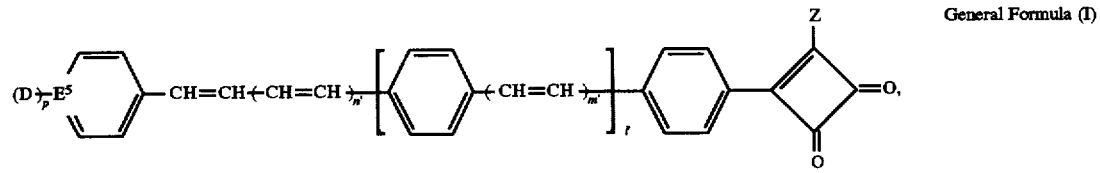

General Formula (I)

which is an (E) form, a (Z) form, or a mixture of the (E) and (Z) forms, wherein Z is a substituent capable of hydrogen-bonding, D is 1 or 0, $E^5$ is a carbon atom or a nitrogen atom, in the case where $E^5$ is a carbon atom, p is 1, D is a substituent having a substituent constant which is 0 or a negative value, in the case where $E^5$ is a nitrogen atom, p is 0, m' is an integer 1 or 2, n' is any one of integers from 0 to 3, l' is any one of integers 0, 1 and 2, and in the case where l' is 2, two m' in the formula may be the same or different from each other.

(iii) A non-linear optical device according to the present invention and having a second order hyperpolarizablity β of 20×10⁻³⁰ esu or higher.

A representative schematic view, description of the same, and a representative manufacturing method will now be described with reference to the following examples.

Examples of the present invention will now be described.

EXAMPLE 1

Preparation of cyclobutenedione derivative (I-1), the raw material of which is 1-(4-iodophenyl)-2-[(r)-2-hydroxypropylamino]-cyclobutene-3,4-dione (II-1) and styrene 3.58 g (10 m mol) of a compound represented by the following structural formula (II-1), 1.8 g (10.5 m mol) of styrene, 0.116 g (0.1 m mol, which was 1% with respect to (II-1)) of tetrakis (triphenylphosphine) palladium and 1.23 g (15 m mol) of sodium acetate were dissolved in 15 ml of N,N-dimethylformamide, and then reaction was allowed to take place for 6 hours at 100° C.

After the reaction was completed, the reaction solution was introduced into water to cause orange crystal to precipitate, followed by filtrating the precipitation. Then, the orange crystal was recrystallized by using N,N-dimethylformamide so that 3.54 g of 1-1-(4"[[2" "-(r)-hydroxypropylamino]cyclobutene-3" ", 4' '-dione-1' '-yl] phenyl)-4-1 (phenyl)-ethylene represented by the following structural formula (I-1) was obtained. The yield was 88%. The obtained crystal was subjected to element analysis, thus resulting in C: 73.87% (74.60%), H: 6.50% (6.51%) and N: 6.91% (7.04%) (note that parenthesized values are calculated values). The melting point was >285° C. (decomposition temperature). The maximum absorption wavelength (λmax) in the methanol solution was 339.5 nm.

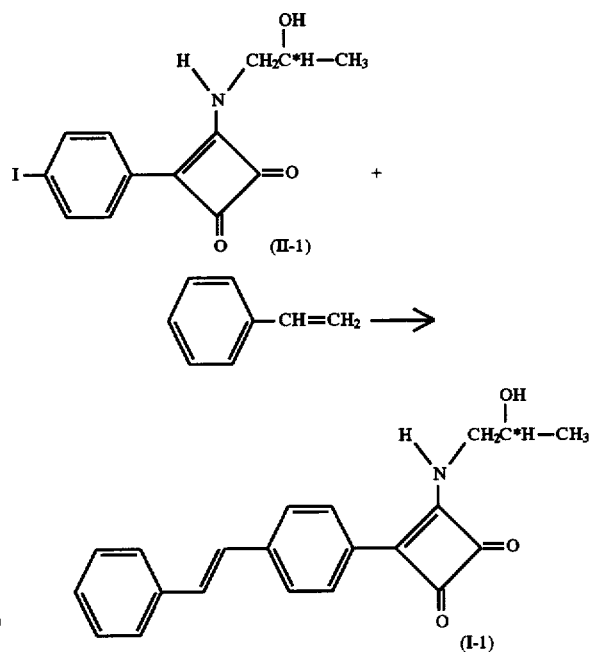

EXAMPLE 2

Preparation of cyclobutenedione derivative (I-2), the raw material of which is 1-(4-bromophenyl)-2-[(r)-2- hydroxypropylamino]-cyclobutene-3,4-dione (II-2) and 4-vinylanisole (III-3)

3.09 g (10 m mol) of a compound represented by the following structural formula (II-2), 1.8 g (10.5 m mol) of 4-vinylanisole (III-3), 0.578 g (0.5 m mol, which was 5% with respect to (II-2)) of tetrakis (triphenylphosphine) palladium and 3.15 g (15 m tool) of 1,8-bis (dimethylamino) naphthalene were dissolved in 15 ml of N,N-dimethylformamide, and then reaction was allowed to take place for 12 hours at 100° C.

After the reactions was completed, the reaction solution was introduced into water to cause orange crystal to precipitate, followed by filtrating the precipitation. Then, the orange crystal was recrystallized by using N,N-dimethylformamide so that 1.17 g of 1-1-(4"[[2" "-(r)-hydroxypropylamino]-cyclobutene-3" ", 4' '-dione-1' '-yl] phenyl)-2-(4' ' '-methoxyphenyl)-ethylene represented by the following structural formula (I-2) was obtained. The yield was 29%. The obtained crystal was subjected to element analysis, thus resulting in C: 72.20% (72.21%), H: 5.81% (5.82%) and N: 3.49% (3.845%) (note that parenthesized values are calculated values). The melting point was >285° C. (decomposition temperature). The maximum absorption wavelength (λmax) in the methanol solution was 400.2 nm.

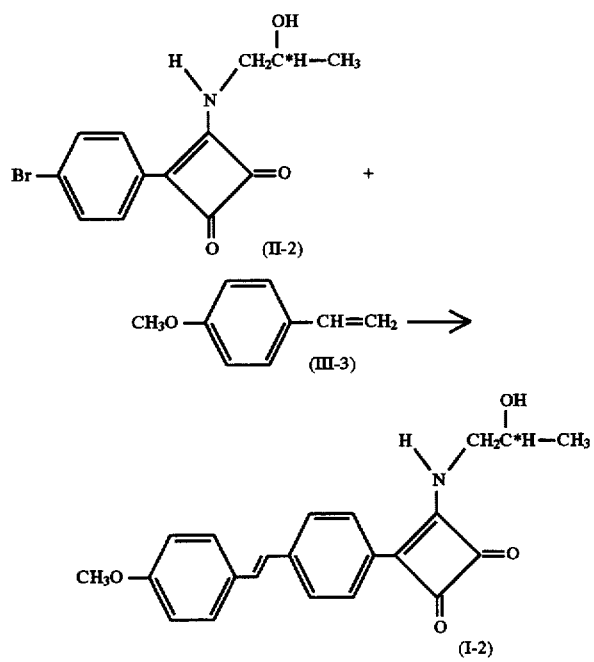

EXAMPLE 3

Preparation of cyclobutenedione derivative (I-3), the raw material of which is 1-(4-bromophenyl)-2-ethoxycyclobutene-3,4-dione and 4-dimethylaminostyrene 3.28 g (10 m mol) of a cyclobutene compound represented by the following structural formula was dissolved in 15 ml of N,N-dimethylformamide. Then, 0.8 g (10 m mol) of (R)-(−)-1-amino-2-propanol was added thereto, and then the solution was stirred at room temperature for 30 minutes. Then, 1.8 g (10.5 m mol) of 4-dimethylaminophenylstyrene, 0.0225 g (0.5 m mol, which was 5% with respect to the cyclobutene compound) of palladium acetate, 0.1218 g (2 m mol, which was four times palladium acetate) of tris (o-tolyl phosphine and 1.23 g (15 m mool ) of sodium acetate were added thereto, and then reaction was caused to take place at 100° C. for four hours.

After the reaction was completed, the reaction solution was introduced into water to cause orange crystal to precipitate, followed by filtrating the precipitation. Then, the orange crystal was recrystallized by using N,N-dimethylformamide so that 2.98 g of 1-1-(4"[[2" "-(r)-hydroxypropylamino]-cyclobutene-3" ", 4' '-dione-1' '-yl] phenyl)-2-1 (4' ' '-dimethylaminophenyl)-ethylene represented by the following structural formula (I-3) was obtained. The yield was 74%. The obtained crystal was subjected to element analysis, thus resulting in C: 73.33% (73.38%), H: 6.430% (6.43%) and N: 7.39% (7.44%) (note that parenthesized values are calculated values). The melting point was >295° C. (decomposition temperature). The maximum absorption wavelength (λmax) in the methanol solution was 420.5 nm.

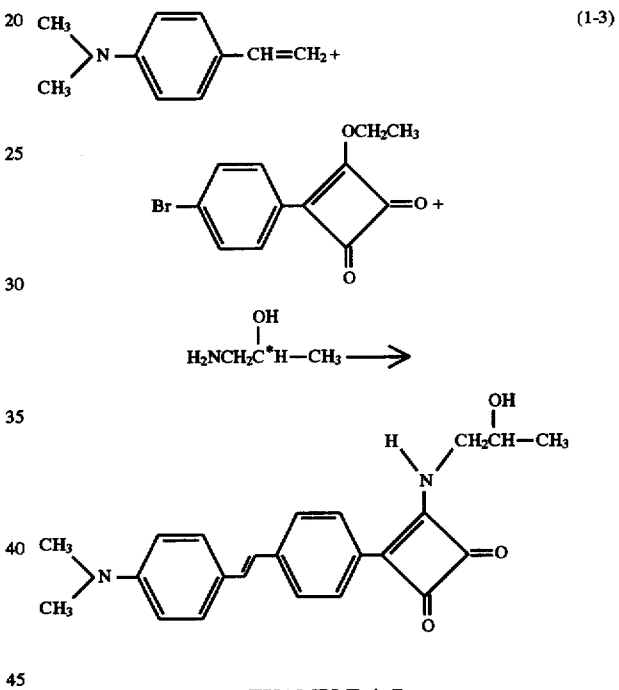

EXAMPLE 4–7

A target compound shown in Tables 1A and 1B was prepared in the same manner as in Example 1–3 except that styrene (III-4)–(III-7) shown in Table 1 was used as an intermediate raw material. The melting point and the maximum absorption wavelength were measured, and then the element analysis was performed, thus obtaining values shown in Table 2.

EXAMPLE 8

Preparation of cyclobutenedione derivative (I'), the raw material of which is 1-(4-iodophenyl)-2-[(r)-2-hydroxypropylamino]-cyclobutene-3,4-dione (III-1)

3.57 g (10 m mol) of a compound represented by the following structural formula (III-1), 1.1 g (10.5 m mol) of 4-vinylpyridine, 0.116 g (0.1 m mol, which was 1% with respect to (III-1)) of tetrakis (triphenylphosphine) palladium and 1.23 g (15 m mol) of sodium acetate were dissolved in 15 ml of N,N-dimethylformamide, and then reaction was allowed to take place for 4 hours at 100° C.

After the reaction was completed, the reaction solution was introduced into water to cause brown crystal to precipitate, followed by filtrating the precipitation. Then, the brown crystal was recrystallized by using N,N-dimethylformamide so that 2.94 g of 1-(4'[2"-(r)-hydroxypropylamino]-cyclobutene-3", 4"-dione-1"-yl] phenyl)-2-(4'''-pyridyl)-ethylene represented by the following structural formula (I') was obtained. The yield was 88%. The obtained crystal was subjected to element analysis, thus resulting in C: 71.56% (71.84%), H: 5.60% (5.43%) and N: 8.11% (8.38%) (note that parenthesized values are calculated values). The melting point was 265° C. to 267° C. (decomposition also took place). The maximum absorption wavelength (λmax) in the methanol solution was 375.5 nm. The diene bond was a trans from.

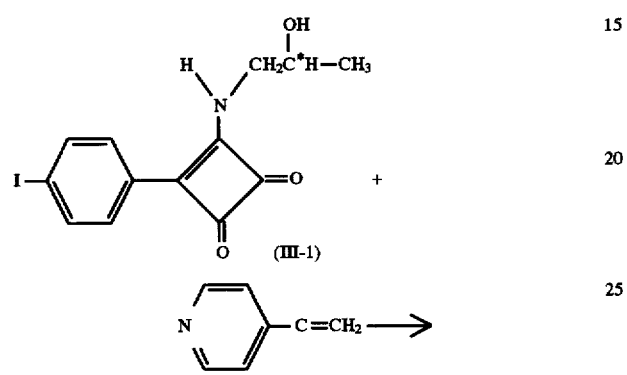

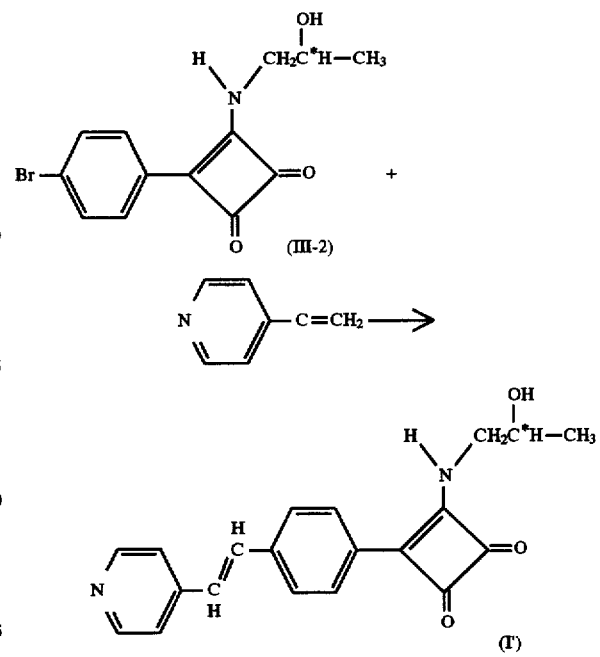

EXAMPLE 9

Preparation of cyclobutenedione derivative (I'), the raw material of which is 1-(4-bromophenyl)-2-[(r)-2-hydroxypropylamino]-cyclobutene-3,4-dione (III-2)

3.10 g (10 m mol) of a compound represented by the foregoing structural formula (III-2), 1.1 g (10.5 m mol) of 4-vinylpyridine, 0.578 g (0.5 m mol, which was 5% with respect to (III-2)) of tetrakis (triphenylphosphine) palladium and 3.21 g (15 m mol) of 1,8-bis (dimethylamino) naphthalene were dissolved in 15 ml of N,N-dimethylformamide, and then reaction was allowed to take place for 6 hours at 120° C.

After the reactions was completed, the reaction solution was introduced into water to cause yellow crystal to precipitate, followed by filtrating the precipitation. Then, the yellow crystal was recrystallized by using N,N-dimethylformamide so that 1.07 g of 1-(4'[2"-(r)-hydroxypropylamino]-cyclobutene-3", 4"-dione-1"-yl] phenyl)-2-(4'''-pyridyl)-ethylene represented by the following structural formula (I') was obtained. The yield was 32%. As a result of the element analysis and measurements of the melting point and the absorbance, a conclusion was made such that the obtained compound was the same as that obtained in the reactions in Example 8.

EXAMPLE 10

Preparation of cyclobutenedione derivative (I'), the raw material of which is 1-(4-iodophenyl)-2-ethoxycyclobutene-3,4-dione (V-1)

3.28 g (10 m mol) of a compound represented by the following structural formula (V-1) was dissolved in 15 ml of N,N-dimethylformamide. Then, 0.8 g (10 m mol) of (R)-(-)-1-amino-2-propanol was added thereto, and then stirred at room temperature for 30 minutes. Then, 1.1 g (10.5 m mol) of 4-vinylpyridine, 0.0225 g (0.5 m mol, which was 5% with respect to (V-1)) of palladium acetate, 0.1218 g (2 m mol, which was four times palladium acetate) of tris (o-tolyl) phosphine and 1.23 g (15 m mol) of sodium acetate were added thereto, and then reaction was allowed to take place for 4 hours at 100° C.

After the reactions was completed, the reaction solution was introduced into water to cause orange crystal to precipitate, followed by filtrating the precipitation. Then, the orange crystal was recrystallized by using N,N-dimethylformamide so that 2.67 g of 1-(4'[2"-(r)-hydroxypropylamino]-cyclobutene-3", 4"-dione-1"-yl] phenyl)-2-(4'''-pyridyl)-ethylene represented by the following structural formula (I') was obtained. The yield was 80%. As a result of the element analysis and measurements of the melting point and the absorbance, a conclusion was made such that the obtained compound was the same as that obtained in the reactions in Example 8.

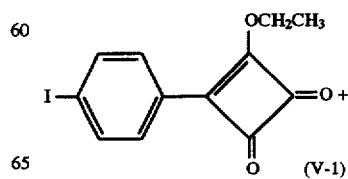

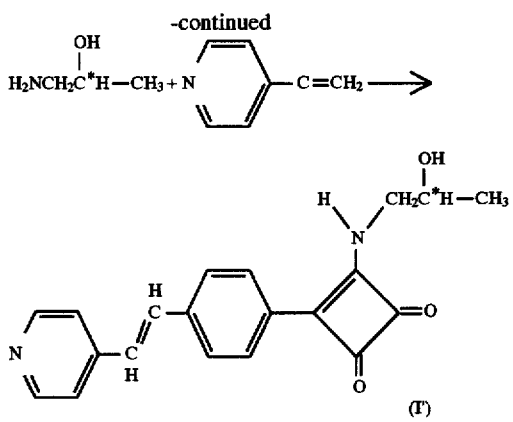

(T)

EXAMPLE 11

Preparation of cyclobutenedione derivative (VIII-1), the raw material of which is 1-(4-iodophenyl)-2-ethoxycyclobutene-3,4-dione (V-1)

3.28 g (10 m mol) of the compound represented by the following structural formula (V-1) was dissolved in 15 ml of N,N-dimethylformamide. Then, 0.8 g (10 m mol) of n-butylamine was added thereto, and then stirred at room temperature for 30 minutes. Then, 1.1 g (10.5 m mol) of 4-vinylpyridine, 0.0225 g (0.5 m mol, which was 5% with respect to (V-1)) of palladium acetate, 0.1218 g (2 m mol, which was four times palladium acetate) of tris (o-tolyl) phosphine and 1.23 g (15 m mol) of sodium atcetate were added thereto, and then reaction was allowed to take place for 4 hours at 100° C.

After the reaction was completed, the reaction solution was introduced into water to cause orange crystal to precipitate, followed by filtrating the precipitation. Then, the orange crystal was recrystallized by using N,N-dimethylformamide so that 2.31 g of 1-(4'[2"-butylamino-cyclobutene-3", 4"-dione-1"-yl] phenyl)-2-(4'''-pyridyl)-ethylene represented by the following structural formula (VIII-1) was obtained. The yield was 70%. The obtained crystal was subjected to element analysis, thus resulting in C: 74.79% (75.08%), H: 6.31% (6.06%) and N: 8.20% (8.43%) (note that parenthesized values are calculated values). The melting point was from 240° C. to 243° C. (decomposition took place). The maximum absorption wavelength (λmax) in the methanol solution was 375.5 nm.

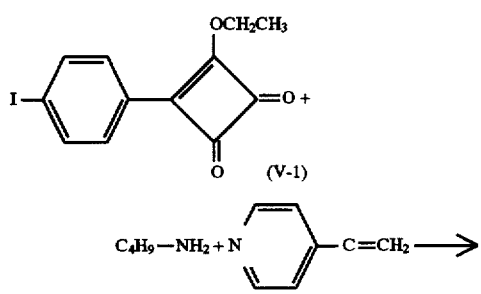

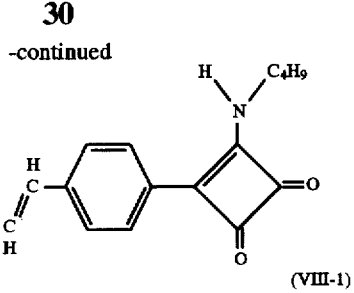

(VIII-1)

EXAMPLE 12

Preparation of cyclobutenedione derivative (VIII-1), the raw material of which is 1-(4-bromophenyl)-2-butylamino-cyclobutene-3,4-dione 3.09 g (10 m mol) of the compound represented by the following structural formula, 1.1 g (10.5 m mol) of 4-vinylpyridine, 0.578 g (0.5 m mol, which was 5% with respect to the cyclobutene) of tetrakis (triphenylphosphine) palladium and 3.15 g (15 m mol) of 1,8-bis (dimethylamino) naphthalene were dissolved in 15 ml of dimethylformamide, and then reaction was allowed to take place at 100° C. for 4 hours.

After the reactions was completed, the reaction solution was introduced into water to cause yellow crystal to precipitate to filtrate the precipitation. Then, the orange crystal was recrystallized by using N,N-dimethylformamide so that 1.65 g of 1-(4'[2"-butylamino-cyclobutene-3", 4"-dione-1"-yl] phenyl)-2-(4'''-pyridyl)-ethylene represented by the foregoing structural formula (VIII-1) was obtained. The yield was 50%. As a result of the element analysis and measurements of the melting point and the absorbance, a conclusion was made such that the obtained compound was the same as that obtained in the reactions in Example 11.

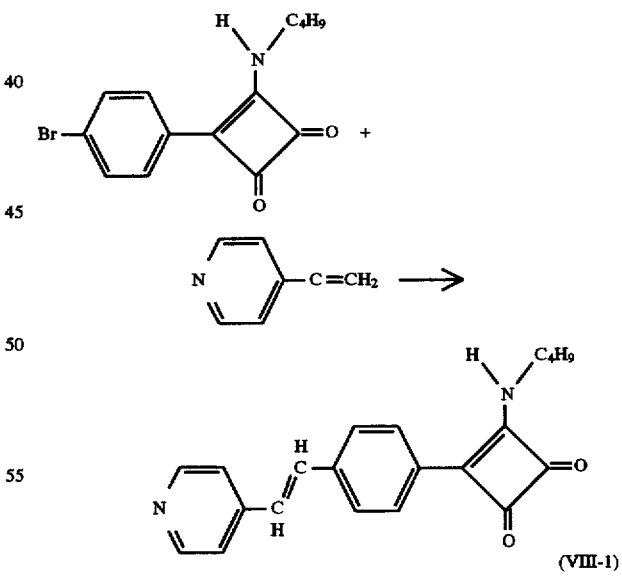

(VIII-1)

EXAMPLE 13

Preparation of cyclobutenedione derivative (II-13), the raw material of which is 1-(4'[2"-butylamino-cyclobutene-3", 4"-dione-1"-yl] phenyl)-2-(4'''-pyridyl)-ethylene (VIII-1)

3.30 g (10 m mol) of a compound represented by the following structural formula (VIII-1) was dissolved in 5 ml of N-methylpyridine, and then 1.64 g (12 m mol) of N-butylbromide was added thereto. Then, reaction was allowed to take place at 120° C. for 4 hours.

After the reaction was completed, generated orange and needle-shape crystal was separated by filtration. The obtained crystal was recrystallized by using methanol so that 4.22 g of 1-(4'[2"-butylamino-cyclobutene-3",4"-dione-1"-yl] phenyl)-2-(4'"-N-butylpyridinium)-ethylenebromide represented by structural formula (I-13) was obtained. The yield was 90%. The obtained crystal was subjected to element analysis, thus resulting in C: 63 33.56% (68.97%), H: 6.52% (6.28%), N: 5.90% (5.97%) and Br: 16.58% (17.02%)(note that parenthesized values are calculated values). The melting point was 265° C. to 267° C. (decomposition also took place). The maximum absorption wavelength (λmax) in the methanol solution was 370.8 nm.

EXAMPLE 14

Preparation of cyclobutenedione derivative (I-8), the raw material of which is 1-(4-iodophenyl)-2-[(r)-2-hydroxypropylamino] cyclobutene-3,4-dione (II-1)

3.58 g (10 m mol) of a compound represented by the following structural formula (II-1), 1.8 g (10.5 m mol) of 1-(4'-dimethylaminophenyl) butadiene (III-1), 0.116 g (0.1 m mol, which was 1% with respect to (II-1)) of tetrakis (triphenylphosphine) palladium and 1.23 g (15 m mol) of sodium acetate were dissolved in 15 ml of N,N-dimethylformamide, and then reaction was allowed to take After the reaction was completed, reaction solution was introduced into water so that orange crystal was deposited and then it was separated by filtration. The precipitation was recrystallized by using N,N-dimethylformamide so that 3.54 g of 1-[4'-{2"-[2'"-(r)-hydroxypropylamino]-cyclobutene-3",4"-dione-1"-yl] phenyl]-4-14""-dimethylaminophenyl)-1, 3-butadiene represented by structural formula (I-8) was obtained. The yield was 88%. The obtained crystal was subjected to element analysis, thus resulting in C: 73.87% (74.60%), H: 6.50% (6.51%) and N: 6.91% (7.04%)(note that parenthesized values are calculated values). The melting point was>285° C. (decomposition also took place). The maximum absorption wavelength (λmax) in the methanol solution was 439.5 nm. The diene bond was cis/trans forms.

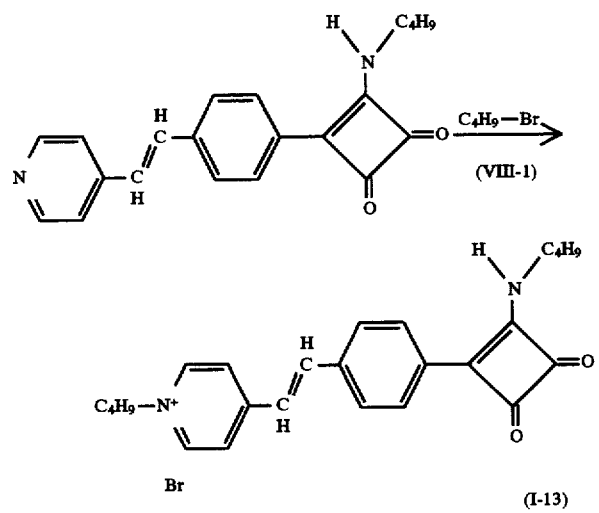

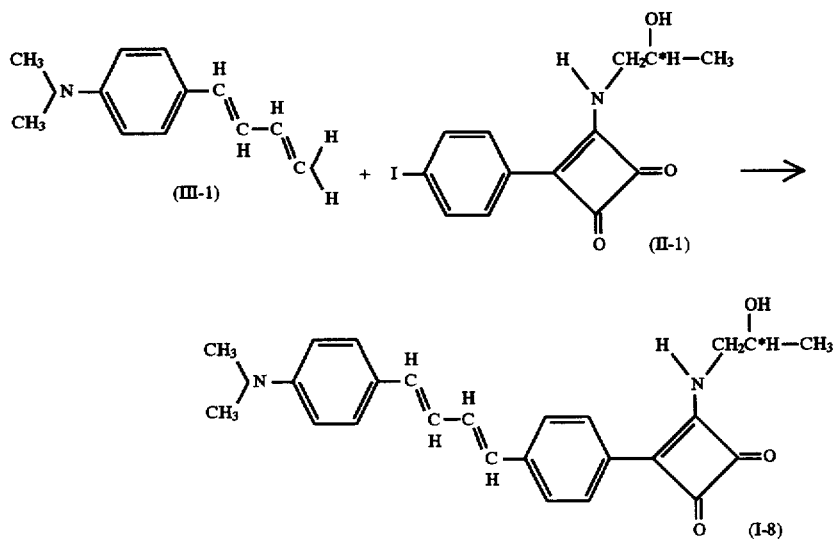

EXAMPLE 15

Preparation of cyclobutenedione derivative (I-8), the raw material or which is 1-(4-bromophenyl)-2-[(r)-2-hydroxypropylamino]-cyclobutene-3,4-dione (II-2)

3.09 g (10 m mol) of a compound represented by the following structural formula (II-2), 1.8 g (10.5 m mol) of 1-(4'-dimethylaminophenyl) butadiene (III-1), 0.578 g (0.5 m mol, which was 5% with respect to (II-2)) of tetrakis (triphenylphosphine) palladium and 3.15 g (15 m mol) of 1,8-bis (dimethylamino) naphthalene were dissolved in 15 ml of N,N-dimethylformamide, and then reaction was allowed to take place at 100° C. for 12 hours.

After the reaction was completed, the reaction solution was introduced into water to cause orange crystal to precipitate followed by separating the precipitation by filtration. Then, the orange crystal was recrystallized by using N,N-dimethylformamide so that 1.17 g of 1-[4'-{2"-[2"'-(r)-hydroxypropylamino]-cyclobutene-3",4"-dione-1"-yl] phenyl]-4-14""-dimethylaminophenyl)-1,3-butadiene represented by the following structural formula (I-8) was obtained. The yield was 29%. As a result of the element analysis and measurements of the melting point and the absorbance, a conclusion was made such that the obtained compound was the same as that obtained in the reactions in Example 14.

(R)-(−)-1-amino-2-propanol was added thereto, and then the solution was stirred at room temperature for 30 minutes. Then, 1.8 g (10.5 m mol) of 1-(4'-dimethylaminophenyl) butadiene (III-1), 0.0225 g (0.5 m mol, which was 5% with respect to (IV-1)) of palladium acetate, 0.1218 g (2 m mol, which was 4 times palladium acetate) of tris (o-tolyl) phosphine and 1.23 g (15 m mol) of sodium acetate were added thereto, and then reaction was allowed to take place at 100° C. for 4 hours.

After the reaction was completed, the reaction solution was introduced into water to cause orange crystal to precipitate, followed by separating the precipitation by filtration. Then, the orange crystal was recrystallized by using N,N-dimethylformamide so that 2.98 g of 1-[4'-{2"-[2"'-(r)-hydroxypropylamino]-cyclobutene-3",4"-dione-1"-yl] phenyl]-4-14""-dimethylaminophenyl)-1,3-butadiene represented by the following structural formula (I-8) was obtained. The yield was 74%. As a result of the element analysis and measurements of the melting point and the absorbance, a conclusion was made such that the obtained compound was the same as that obtained in the reactions in Example 14.

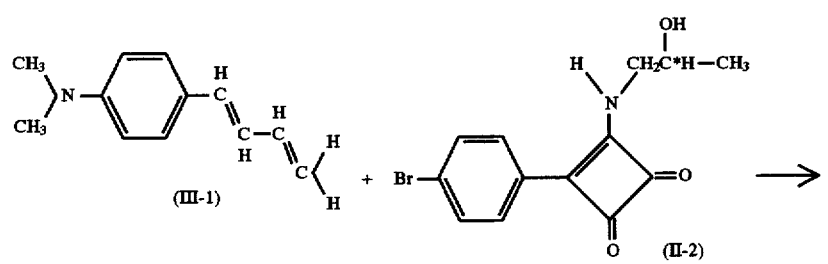

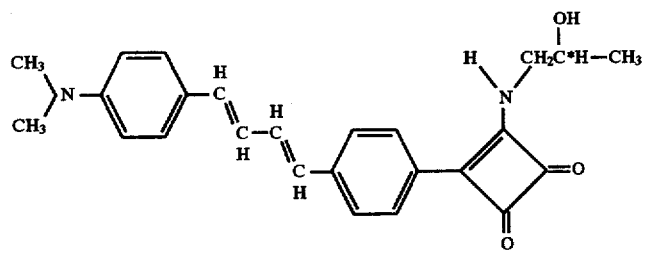

EXAMPLE 16

Preparation of cyclobutenedione derivative (I-8), the raw material of which is 1-(4-iodophenyl)-2-ethoxycyclobutene-3,4-dione (IV-1)

3.28 g (10 m mol) of a compound represented by the following structural formula (IV-1) was dissolved in 15 ml of N,N-dimethylformamide. Then, 0.8 g (10 m mol) of

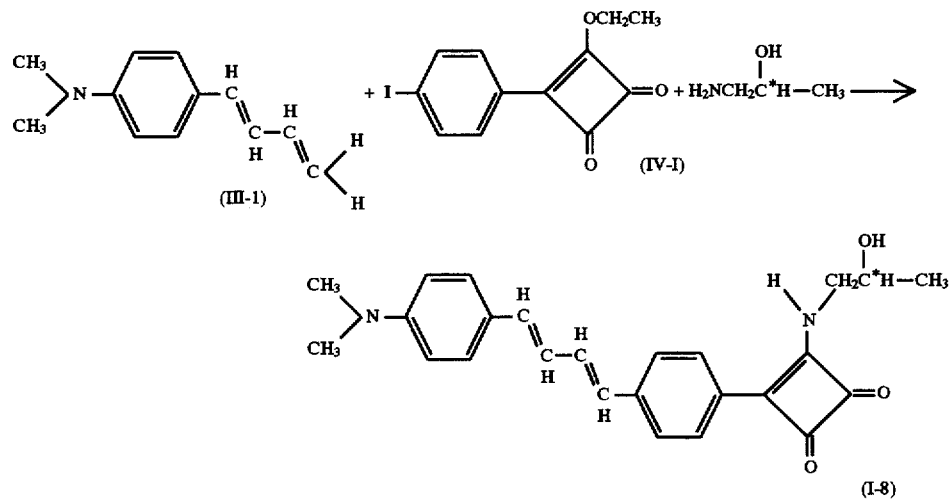

EXAMPLE 17

The second order hyperpolarizability β of 1-[4'-{2"-[2"'-(r)-hydroxypropylamino]-cyclobutene-3",4"-dione-1"-yl] phenyl]-4-14""'-dimethylaminophenyl)-1,3-butadiene [Structural formula (I-8)] prepared in Example 14 was measured. The measurement was performed by a Hyper-Rayleigh scattering method [Phys. Rev. Lett., 66,2980 (1991)] suggested by K. Cray and A. Persons et. al., the measurement being performed in methanol. A value of β of $1700 \times 10^{-30}$ esu was obtained. On the other hand, a similar measurement was performed by using, as a sample, p-nitroaniline and 1-(4-dimethylaminophenyl)-2-[2-(r)-hydroxypropylamino]-cyclobutene-3,4-dione [structural formula (VII-1)], thus resulting in β being $35 \times 10^{-30}$ esu and $140 \times 10^{-30}$ esu.

EXAMPLE 18

The second order hyperpolarizability β of 1-(4'[2"-(r)-hydroxypropylamino]-cyclobutene-3", 4"-dione-1"-yl] phenyl)-2-(4"'-pyridyl)-ethylene [Structural formula (I')] prepared in Example 8 was measured. The measurement was performed by a Hyper-Rayleigh scattering method [Phys. Rev. Lett., 66,2980 (1991)] suggested by K. Gray and A. Persons et. al., the measurement being performed in methanol. A value of β of $500 \times 10^{-30}$ esu was obtained.

EXAMPLE 19

The second order hyperpolarizability β of 1-(4'[2"-butylamino-cyclobutene-3",4"-dione-1"-yl]phenyl)-2-(4"'-N-butylpyridium)-ethylenebromide [structural formula (I-13) prepared in Example 13 was measured. The measurement was performed similarly to Example 17. Thus, obtained value was $470 \times 10^{-30}$ esu.

EXAMPLE 20

The second order hyperpolarizability β of each of the compounds prepared in Examples 1 to 7 was measured similar to Example 17. Results are shown in Table 2, with the result of the cyclobutenedione prepared in Example 14. Measurement of SHG activity:

EXAMPLE 21

Powder of 1-[4'-{2"-[2"'-(r)-hydroxypropylamimo]-cyclobutene-3",4"-dione-1"-yl] phenyl]-4-14""'-dimethylaminophenyl)-1,3-butadiene prepared in Example 14 was filled in a glass cell, and then irradiated with Nd dope YAG laser (wavelength was 1.064 μm and output was 180 mJ/pulse). As a result, green scattered light having a wavelength of 532 nm, which was a secondary harmonic wave of the laser, was generated. Its intensity was about 30 times that measured when urea powder was used as a sample.

EXAMPLE 22

Powder of 1-(4'[2"-(r)-hydroxypropylamino]-cyclobutene-3",4"-dione-1"-yl] phenyl)-2-(4"'-pyridyl)-ethylene [structural formula (I')] prepared in Example 8 was filled in a glass cell, and then irradiated with Nd dope YAG laser (wavelength was 1.064 μ and output was 180 mJ/pulse). As a result, green scattered light having a wavelength of 532 nm, which was a secondary harmonic wave of the laser, was generated. Its intensity was about 30 times that measured when urea powder was used as the sample.

EXAMPLE 23

Powder of 1-(4'[2"-butylamino-cyclobutene-3",4"-dione-1"-yl] phenyl)-2-(4"'-N-butylpyridinium)-ethylenebromide [structural formula (I-13)] prepared in Example 13 was filled in a glass cell, and then irradiated with Nd dope YAG laser (wavelength was 1.064 μm and output was 180 mJ/pulse). As a result, green scattered light having a wavelength of 532 nm, which was a secondary harmonic wave of the laser, was generated. Its intensity was about 25 times that measured when urea powder was used as a sample.

EXAMPLE 24

About the cyclobutene derivatives prepared in Examples 1–7, the non-linear property (SHG activity) of samples thereof was measured. Results are shown in Table 3, with the result of the cyclobutene prepared in Example 14. Values of SHG activity are those on the basis of the value obtained by using urea as a sample.

As seen from Table 3, the cyclobutenedione derivatives according to the invention exhibited a higher second order hyperpolarizability (β) and non-linear optical property (SHG activity) than know organic non-linear optical materials and were useful for organic non-linear optical materials. In particular, the compounds (I-3) and (I-8), which have $N(CH_3)_2$ as a subsutituent of D, were excellent.

As above, the cyclobutenedione derivatives according to the invention have higher second order hyperpolarizability and non-linear property (SHG activity) than known organic non-linear optical materials.

FIG. 1 is a block diagram showing an optical system employed to measure the non-linear characteristic (the SHG activity). A sample 12 is irradiated with a light beam having a wavelength of 1.064 μm emitted from a Nd dope YAG laser beam unit 11. Green scattered light having a wavelength of 532 nm from the sample 12 is introduced into a photoelectron sensiticizer 16 through a lens 13, a filter 14 and a monochrome meter 15 so that the intensity of green scattered light is measured.

TABLE IA

| COMPOUND (III) | CYCLOBUTENEDIONE DERIVATIVES (I) |
|---|---|
| 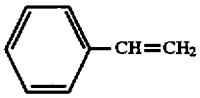<br>(II-1) | 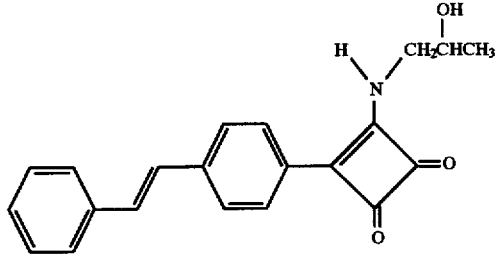<br>(I-1) |
| 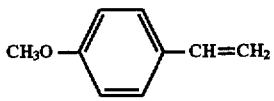<br>(II-2) | 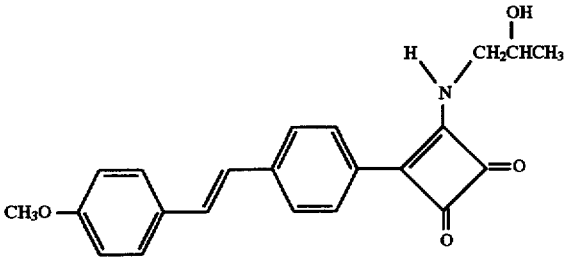<br>(I-2) |
| 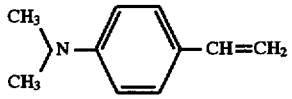<br>(III-3) | 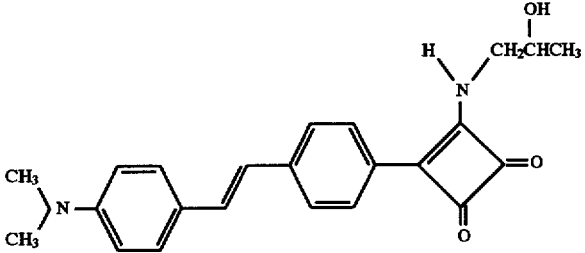<br>(I-3) |
| 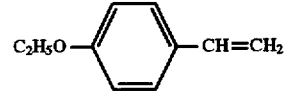<br>(II-4) | 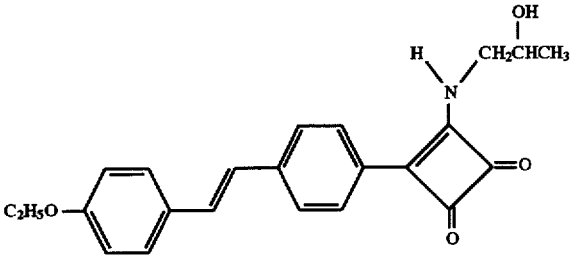<br>(I-4) |

TABLE 1B

| COMPOUND (III) | CYCLOBUTENEDIONE DERIVATIVES (I) |
|---|---|
| (III-5) nC₃H₇O-C₆H₄-CH=CH₂ | (I-5) |
| (III-6) (CH₃)₃CO-C₆H₄-CH=CH₂ | (I-6) |
| (III-7) Cl-C₆H₄-CH=CH₂ | (I-7) |

TABLE 2

| | YIELD (%) | M.P. (°C.) | ELEMENTAL ANALYSIS (CALC.) C | H | N | Cl | λmax (in MeOH) |
|---|---|---|---|---|---|---|---|
| (I-1) | 88 | 288–* | 73.87 (74.60) | 6.50 (6.51) | 6.91 (7.04) | — | 339.5 |
| (I-2) | 29 | 285–* | 72.70 (72.71) | 5.81 (5.82) | 3.49 (3.85) | — | 400.2 |
| (I-3) | 74 | 295–* | 73.33 (73.38) | 6.43 (6.43) | 7.39 (7.44) | — | 420.5 |
| (I-4) | 53 | 283–* | 73.09 (73.19) | 6.11 (6.14) | 3.59 (3.71) | — | 400.5 |
| (I-5) | 58 | 280–* | 73.55 (73.64) | 6.39 (6.44) | 3.50 (3.58) | — | 400.2 |
| (I-6) | 51 | 277–* | 72.83 (74.05) | 6.90 (6.71) | 3.27 (3.45) | — | 398.7 |
| (I-7) | 72 | 284–* | 68.11 (68.57) | 4.27 (4.93) | 3.59 (3.81) | 9.29 (9.64) | 373.0 |
| (I-8) | 88 | 288–* | 73.87 (74.60) | 6.50 (6.51) | 6.91 (7.04) | — | 439.5 |

*With decomposition

TABLE 3

| CYCLOBUTENEDIONE DERIVATIVES | β (×10⁻³⁰ esu) | SHG ACTIVITY (TO UREA) |
|---|---|---|
| STRUCTURE (I-1) EXAMPLE 1 | 320 | 20 |
| STRUCTURE (I-2) EXAMPLE 2 | 400 | 60 |
| STRUCTURE (I-3) EXAMPLE 3 | 750 | 50 |
| STRUCTURE (I-4) EXAMPLE 4 | 400 | 60 |
| STRUCTURE (I-5) EXAMPLE 5 | 390 | 50 |
| STRUCTURE (I-6) EXAMPLE 6 | 380 | 10 |
| STRUCTURE (I-7) EXAMPLE 7 | 280 | 15 |
| STRUCTURE (I-8) EXAMPLE 14 | 1700 | 30 |

What is claimed is:

1. A cyclobutenedione compound comprising:

substituted or non-substituted aromatic group A; conjugated chain B; and hydrogen bonding or ion bonding cyclobutenedionyl substituted group C having an aromatic group which is bonded to the conjugated chain B, wherein A and B and C are bonded in the form of A—B—C.

2. A cyclobutenedione compound according to claim 1, wherein said substituted or non-substituted aromatic group A is represented by the following Formula (A1):

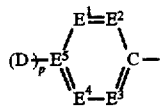

wherein $E^1$ to $E^5$ are each independently a nitrogen atom, or a carbon atom which may have a substituent, at least two of $E^1$ to $E^5$ are carbon atoms, in a case where adjacent $E^1$ and $E^2$ or adjacent $E^3$ and $E^4$ are carbon atoms each having a substituent, the substituents may be bonded to each other to form a ring, p is 1 or 0, in the case where $E^5$ is a carbon atom, p is 1, D is a substituent having a Hammett substituent constant $\delta_0{}^R$ which is 0 or a negative value in the case where $E^5$ is a nitrogen atom, p is 0 or 1, in the case where p is 1, D is a substituted or a non-substituted alkyl group, and in this case the nitrogen indicated by $E^5$ is positively charged, and thus an ion having a negative charge is present as a counter ion.

3. A cyclobutenedione compound according to claim 1, wherein the conjugated chain B contains at least one molecular structure selected from the group represented by the following formulas:

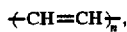

which is an (E) form, a (Z) form, or a mixture of the (E) and (Z) forms

-continued

which is an (E) form, a (Z) form, or a mixture of the (E) and (Z) forms

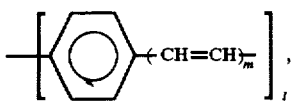

which is an (E) form, a (Z) form, or a mixture of the (E) and (Z) forms, wherein m, n and l are each independently the number of bonding units of the conjugated chain.

4. A cyclobutenedione compound according to claim 1, wherein the hydrogen bonding or ion bonding cyclobutenedionyl group C having an aromatic group which is bonded to the conjugated chain B is represented by the following Formula (C1):

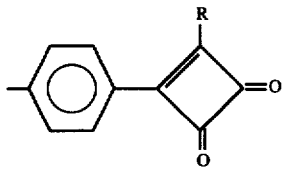

where R is a group represented by the following formula:

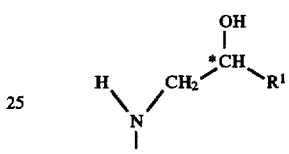

wherein $R^1$ is an alkyl group having 1 to 4 carbon atoms and C* is an asymmetric carbon atom.

5. A cyclobutenedione compound according to claim 1, which is represented by the following Formula (I):

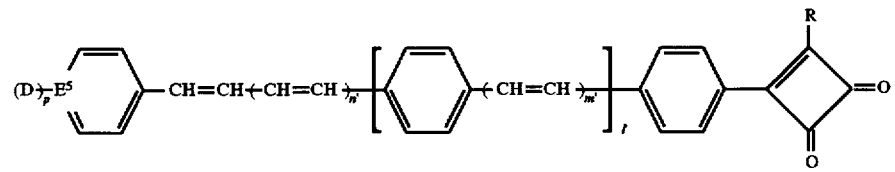

wherein p is 1 or 0, $E^5$ is a carbon atom or a nitrogen atom, in the case where $E^5$ is a carbon atom, p is 1, D is a substituent having a Hammett substituent constant $\delta_0{}^R$ which is 0 or a negative value, in the case where $E^5$ is a nitrogen atom, p is 0, R is a group represented by the following formula, m' is an integer 1 or 2, n' is any one of integers from 0 to 3, l' is any one of integers 0, 1 and 2, in the case where l' is 2, two m' in the formula may be the same or different from each other, and the geometric configuration of the double bond is an (E) form, a (Z) form, or a mixture of the (E) and (Z) forms,

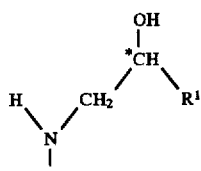

wherein $R^1$ is an alkyl group having 1 to 4 carbon atoms and $C^*$ is an asymmetric carbon atom.

6. A cyclobutenedione compound according to claim 1, which is represented by the following Formula (1a):

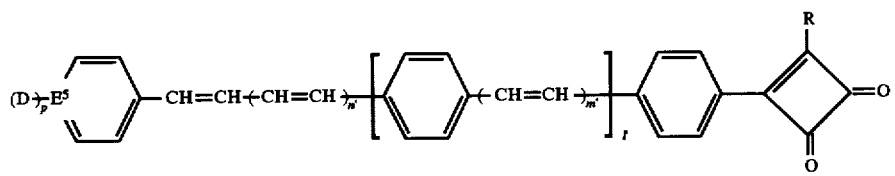

wherein p is 1 or 0, $E^5$ is a carbon atom or a nitrogen atom, in the case where $E^5$ is a carbon atom, p is 1, D is a substituent having a Hammett substituent constant $\delta_0^R$ which is 0 or a negative value, in the case where $E^5$ is a nitrogen atom, p is 0, R is a group represented by the following formula, m' is an integer 1 or 2, n' is any one of integers from 0 to 3, l is any one of integers 0, 1 and 2, in the case where l' is 2, two m' in the formula may be the same or different from each other, and the geometric configuration of the double bond is an (E) form, a (Z) form, or a mixture of the (E) and (Z) forms,

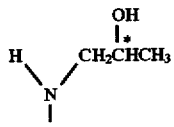

wherein $C^*$ is an asymmetric carbon atom.

7. A cyclobutenedione compound according to claim 1, wherein said cyclobutenedione compound is represented by the following Formula (II):

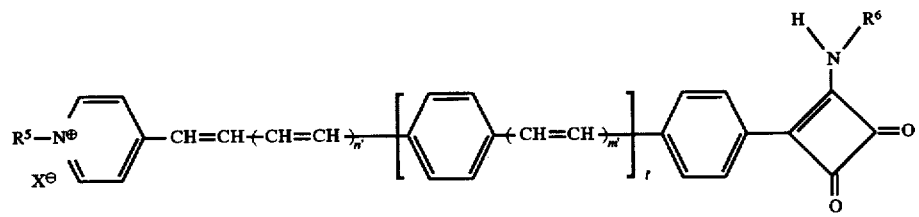

wherein $E^5$ and $E^6$ are each independently an alkyl group having 1 to 4 carbon atoms, X is a halogen atom, m' is an integer 1 or 2, n' is any one of integers from 0 to 3, l' is any one of integers 0, 1 and 2, in the case where l' is 2, two m' in the formula may be the same or different from each other, and the geometric configuration of the double bond is an (E) form, a (Z) form, or a mixture of the (E) and (Z) forms.

8. A cyclobutenedione compound according to claim 1, which is represented by the following formula:

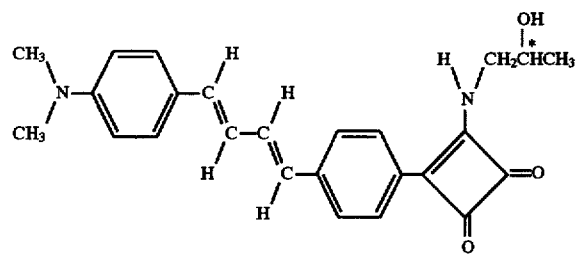

wherein C* is an asymmetric carbon atom.

9. A cyclobutenedione compound according to claim 1, which is represented by the following formula:

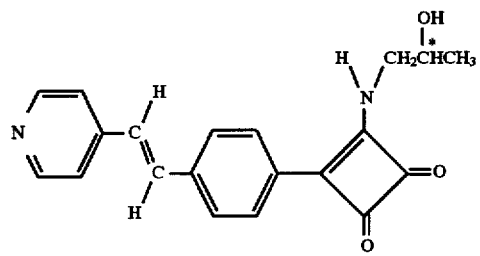

wherein C* is an asymmetric carbon atom.

10. A cyclobutenedione compound according to claim 1, wherein the conjugated chain B has an aromatic bonding group which is different from the aromatic bonding group of the hydrogen bonding or ion bonding substituted cyclobutenedionyl group C.

* * * * *